United States Patent
Tajima

(10) Patent No.: US 9,117,315 B2
(45) Date of Patent: Aug. 25, 2015

(54) RADIOGRAPHIC IMAGE DISPLAY DEVICE AND METHOD FOR DISPLAYING RADIOGRAPHIC IMAGE

(71) Applicant: FUJIFILM Corporation, Tokyo (JP)

(72) Inventor: Takashi Tajima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 297 days.

(21) Appl. No.: 13/933,364

(22) Filed: Jul. 2, 2013

(65) Prior Publication Data

US 2013/0293464 A1 Nov. 7, 2013

Related U.S. Application Data

(63) Continuation of application No. PCT/JP2012/050152, filed on Jan. 6, 2012.

(30) Foreign Application Priority Data

Jan. 13, 2011 (JP) .................................. 2011-004453

(51) Int. Cl.
| | |
|---|---|
| *G06F 3/033* | (2013.01) |
| *G09G 5/08* | (2006.01) |
| *G06T 15/60* | (2006.01) |
| *A61B 6/02* | (2006.01) |
| *A61B 6/12* | (2006.01) |
| *A61B 6/00* | (2006.01) |

(52) U.S. Cl.
CPC ................ *G06T 15/60* (2013.01); *A61B 6/022* (2013.01); *A61B 6/12* (2013.01); *A61B 6/463* (2013.01); *A61B 6/502* (2013.01)

(58) Field of Classification Search
CPC . G06F 3/038; G06F 3/03313; G06F 3/03333; G06F 1/169; G06F 3/0332
USPC .......... 345/156–158, 173–179, 204; 382/128, 382/132, 159
See application file for complete search history.

(56) References Cited

U.S. PATENT DOCUMENTS

| | | | |
|---|---|---|---|
| 2005/0152592 A1* | 7/2005 | Kasai | 382/132 |
| 2005/0169517 A1* | 8/2005 | Kasai | 382/159 |
| 2006/0177115 A1* | 8/2006 | Fujita et al. | 382/128 |
| 2006/0222222 A1* | 10/2006 | Fujita et al. | 382/128 |
| 2009/0097730 A1* | 4/2009 | Kasai et al. | 382/132 |

(Continued)

FOREIGN PATENT DOCUMENTS

| | | |
|---|---|---|
| EP | 1 047 018 A1 | 10/2000 |
| JP | 4-16896 A | 1/1992 |

(Continued)

*Primary Examiner* — Kimnhung Nguyen
(74) *Attorney, Agent, or Firm* — Birch, Stewart, Kolasch & Birch, LLP

(57) ABSTRACT

When displaying a stereo image of radiographic images, troublesome work for indicating an abnormal shadow with a three-dimensional cursor is reduced. An abnormal shadow detection unit 8c detects abnormal shadows from radiographic images for left and right eyes for displaying a stereo image. When a plurality of abnormal shadows are detected, an abnormal shadow specification unit 8d specifies abnormal shadows corresponding to each other in two radiographic images. A display control unit 8e gives a three-dimensional cursor to a predetermined abnormal shadow of the plurality of abnormal shadows, and displays a stereo image using the radiographic images for left and right eyes.

20 Claims, 14 Drawing Sheets

(56) References Cited

U.S. PATENT DOCUMENTS

| | | | |
|---|---|---|---|
| 2009/0169075 A1* | 7/2009 | Ishida et al. | 382/128 |
| 2010/0119041 A1* | 5/2010 | Ohara | 378/87 |
| 2013/0148326 A1* | 6/2013 | Goldfain | 362/19 |
| 2013/0201198 A1* | 8/2013 | Nagatsuka et al. | 345/581 |

FOREIGN PATENT DOCUMENTS

| | | | |
|---|---|---|---|
| JP | 8-294479 A | 11/1996 |
| JP | 9-187446 A | 7/1997 |
| JP | 10-97624 A | 4/1998 |
| JP | 2000-350722 A | 12/2000 |
| JP | 2004-337200 A | 12/2004 |
| JP | 2005-136726 A | 5/2005 |
| JP | 2007-215727 A | 8/2007 |
| JP | 2010-131171 A | 6/2010 |
| JP | 2010-137004 A | 6/2010 |

* cited by examiner

RADIOGRAPHIC IMAGE DISPLAY DEVICE AND METHOD FOR DISPLAYING RADIOGRAPHIC IMAGE

CROSS REFERENCE TO RELATED APPLICATIONS

This application is a Continuation of PCT International Application No. PCT/JP2012/050152 filed on Jan. 6, 2012, which claims priority under 35 U.S.C. §119(a) to Patent Application No. 2011-004453 filed in Japan on Jan. 13, 2011, all of which are hereby expressly incorporated by reference into the present application.

BACKGROUND OF THE INVENTION

1. Field of the Invention

The present invention relates to a radiographic image display device and method for displaying a stereo image of a subject.

2. Description of the Related Art

In an examination at a hospital, a piece of tissue around the lesion may be collected. In recent years, as a method for collecting a piece of tissue without putting a large burden on the patient, a biopsy to puncture the patient with a hollow needle for tissue collection (hereinafter, referred to as a biopsy needle) and collect the tissue embedded in the cavity of the needle has been drawing attention. In addition, a stereo biopsy device has been proposed as a device for performing such a biopsy.

This stereo biopsy device is intended to acquire a plurality of radiographic images with parallax by irradiating a subject from different directions and display a stereo image based on these radiographic images. Since a three-dimensional position of a lesion can be specified while observing the stereo image, a piece of tissue can be collected from a desired position by controlling the tip of the biopsy needle to reach the specific position.

Meanwhile, in the medical field, a computer aided image diagnosis system (CAD: computer aided diagnosis) to automatically detect an abnormal shadow in an image and perform highlighting or the like of the detected abnormal shadow is known. A doctor interprets the image including the abnormal shadow detected by the CAD system, and finally determines whether or not the abnormal shadow in the image is an abnormal shadow indicating a lesion, such as a tumor or calcification.

As a method for detecting an abnormal shadow, for example, a method for automatically detecting the candidate of a tumor shadow (a form of an abnormal shadow), which is a form of cancer or the like, by performing image processing on a radiographic image of the breast or chest using an iris filter and performing thresholding of the output value (refer to JP1998-97624A (JP-H10-97624A)) or a method for automatically detecting the candidate of a micro-calcification shadow (a form of an abnormal shadow), which is another form of breast cancer or the like, by performing image processing using a morphology filter and performing thresholding of the output value (refer to JP 1996-294479A (JP-H08-294479A)) is known.

Incidentally, since the radiographic image is a transmission image inside the subject, structures, such as bones, various tissues, and lesions including tumors or calcification, inside the subject are included in the radiographic image in a state overlapping each other. For this reason, when displaying a stereo image of the radiographic image, an instruction, such as designating an abnormal shadow, is given on the stereo image using a three-dimensional cursor that can move not only in a planar direction but also in a depth direction.

Here, in order to make it easier to visually recognize the detected abnormal shadow, a method for automatically giving a mark, such as an arrow, to the abnormal shadow has been proposed (refer to JP2007-215727A). In addition, a method for giving a mark, such as an arrow, to the abnormal shadow detected by CAD in a plurality of radiographic images for displaying a stereo image and specifying an abnormal shadow of the other image corresponding to the abnormal shadow designated in one image and also giving a warning when an abnormal shadow cannot be detected in the other image has been proposed (refer to JP2010-137004A). In addition, a method for detecting an abnormal shadow from a plurality of radiographic images for three-dimensional display and giving a mark stereoscopically by giving parallax to the plurality of radiographic images when giving a mark such that the detected abnormal shadows match each other has been proposed (refer to JP2004-337200A).

When a plurality of abnormal shadows are detected from radiographic images for displaying a stereo image, a stereo image can be displayed together with marks by giving the marks to the plurality of abnormal shadows using the methods disclosed in JP2010-137004A and JP2004-337200A. Here, when designating an abnormal shadow using a three-dimensional cursor instead of a mark, the operator needs to match the position of the abnormal shadow in the depth direction with the position of the abnormal shadow in the planar direction. However, matching the sense of depth of the three-dimensional cursor with the sense of depth of the abnormal shadow in a stereo image is very troublesome work.

In particular, in the case of stereo biopsy, the stereoscopic effect of a stereo image is larger than the stereoscopic effect of a normal stereo image. Therefore, continuously watching such a stereo image with a large stereoscopic effect in order to match the stereoscopic effect of the three-dimensional cursor with the stereoscopic effect of the abnormal shadow makes the eyes of the operator very tired.

In addition, in the method disclosed in JP2004-337200A, when matching the detected abnormal shadows between radiographic images, abnormal shadows that do not correspond to each other geometrically are eliminated in consideration of the parallax between the radiographic images. Then, the minimum value of the distance between the detected abnormal shadows is calculated between the radiographic images, and abnormal shadows that can be regarded as the most equal abnormal shadows based on the minimum value are matched with each other.

However, in the method disclosed in JP2004-337200A, as shown in FIG. 10, when abnormal shadows B1 and B2 are present, they are included as abnormal shadows BL1 and BL2 and abnormal shadows BR1 and BR2 in a radiographic image for a left eye GL and a radiographic image for a right eye GR acquired at two radiation source positions PL and PR, respectively. If the positions of the abnormal shadows B1 and B2 in a direction perpendicular to the plane (Y direction) are the same, however, it is not possible to specify to which of the abnormal shadows BR1 and BR2 the abnormal shadow BL1 corresponds and to which of the abnormal shadows BR1 and BR2 the abnormal shadow BL2 corresponds on the image.

Thus, unless abnormal shadows can be matched with each other, the same mark cannot be given to corresponding abnormal shadows. In particular, in a stereo biopsy, the tip of the biopsy needle cannot be made to reach the position of the abnormal shadow accurately.

SUMMARY OF THE INVENTION

The present invention has been made in view of the above situation, and it is an object of the present invention to reduce the troublesome work for indicating an abnormal shadow with a three-dimensional cursor when displaying a stereo image of radiographic images.

A radiographic image display device according to the present invention includes: an abnormal shadow detection unit that detects an abnormal shadow from each of two radiographic images acquired by radiographing a subject from two different directions in order to display a stereo image; a display unit that displays the stereo image; a display control unit that, when a plurality of the abnormal shadows are detected, displays a cursor in a three-dimensional manner at a position of a predetermined abnormal shadow of the plurality of abnormal shadows; and an input unit that receives an instruction to change a position of the cursor. The cursor display control unit moves the cursor to each position of the plurality of abnormal shadows sequentially in response to the instruction to change the position of the cursor.

In addition, the radiographic image display device according to the present invention may further include an abnormal shadow specification unit that specifies abnormal shadows corresponding to each other, of the plurality of abnormal shadows detected in the two radiographic images, based on the two radiographic images.

In addition, in the radiographic image display device according to the present invention, the abnormal shadow specification unit may determine whether or not the corresponding abnormal shadows can be specified based on the two radiographic images. The abnormal shadow detection unit may detect an abnormal shadow from a third radiographic image, which has a different radiographing direction from the two radiographic images, when the corresponding abnormal shadows cannot be specified. The abnormal shadow specification unit may specify the corresponding abnormal shadows based on positional relationship of abnormal shadows in the two radiographic images and the third radiographic image.

In addition, the radiographic image display device according to the present invention may further include a warning unit that gives warning of acquisition of the third radiographic image when the abnormal shadow specification unit cannot specify the corresponding abnormal shadows based on the two radiographic images.

In addition, in the radiographic image display device according to the present invention, the abnormal shadow specification unit may specify a position, at which the abnormal shadow can be present, in the subject from positions of abnormal shadows in the two radiographic images and a position of a radiation source when the two radiographic images are acquired, specify a straight line connecting the position of the radiation source and the position of the abnormal shadow in the third radiographic image from the position of the abnormal shadow in the third radiographic image and the position of the radiation source when the third radiographic image is acquired, and specify the corresponding abnormal shadows according to whether or not a position at which the abnormal shadow can be present is present on the straight line.

In addition, in the radiographic image display device according to the present invention, when the two radiographic images are radiographic images of a breast radiographed in order to perform a stereo biopsy, the third radiographic image may be acquired by scout radiographing of a biopsy.

In addition, in the radiographic image display device according to the present invention, the predetermined abnormal shadow may be an abnormal shadow satisfying at least one condition of an abnormal shadow located in a middle of the radiographic image, an abnormal shadow of a specific type, a plurality of dense abnormal shadows (for example, a calcification group), and an abnormal shadow obtained from a predetermined detection result by the abnormal shadow detection unit.

In this case, when the two radiographic images are radiographic images of a breast radiographed in order to perform a stereo biopsy, the predetermined abnormal shadow may be an abnormal shadow present in a range where a biopsy can be acquired by the stereo biopsy.

A radiographic image display method according to the present invention includes: detecting an abnormal shadow from each of two radiographic images acquired by radiographing a subject from two different directions in order to display a stereo image; displaying the stereo image while displaying a cursor in a three-dimensional manner at a position of a predetermined abnormal shadow of the plurality of abnormal shadows when a plurality of the abnormal shadows are detected; receiving an instruction to change a position of the cursor; and moving the cursor to each position of the plurality of abnormal shadows sequentially in response to the instruction to change the position of the cursor.

Another radiographic image display device according to the present invention includes: an abnormal shadow detection unit that detects an abnormal shadow from each of two radiographic images, which are acquired by radiographing a subject from two different directions in order to display a stereo image, and a third radiographic image having a different radiographing direction from the two radiographic images; a display unit capable of displaying one of the two radiographic images and the stereo image; a display control unit that displays one of the two radiographic images on the display unit; an input unit that receives designation of a desired abnormal shadow in the one radiographic image; and an abnormal shadow specification unit that specifies an abnormal shadow, which corresponds to the designated abnormal shadow, in the other radiographic image, which is different from the one radiographic image, based on positional relationship of abnormal shadows in the two radiographic images and the third abnormal shadow. The display control unit displays the stereo image while displaying a cursor in a three-dimensional manner at a position of the designated abnormal shadow.

In addition, in another radiographic image display device according to the present invention, the abnormal shadow specification unit may determine whether or not the corresponding abnormal shadows can be specified based on the two radiographic images. The abnormal shadow detection unit may detect an abnormal shadow from the third radiographic image when the corresponding abnormal shadows cannot be specified. The abnormal shadow specification unit may specify the corresponding abnormal shadows based on positional relationship of abnormal shadows in the two radiographic images and the third radiographic image.

In addition, in another radiographic image display device according to the present invention, when the two radiographic images are radiographic images of a breast radiographed in order to perform a stereo biopsy, the third radiographic image may be acquired by scout radiographing of a biopsy.

In addition, another radiographic image display device according to the present invention may further include a warning unit that gives warning of acquisition of the third radiographic image when the abnormal shadow specification unit cannot specify the corresponding abnormal shadows based on the two radiographic images.

In addition, in another radiographic image display device according to the present invention, the abnormal shadow specification unit may specify a position, at which the abnormal shadow can be present, in the subject from positions of abnormal shadows in the two radiographic images and a position of a radiation source when the two radiographic images are acquired, specify a straight line connecting the position of the radiation source and the position of the abnormal shadow in the third radiographic image from the position of the abnormal shadow in the third radiographic image and the position of the radiation source when the third radiographic image is acquired, and specify the corresponding abnormal shadows according to whether or not a position at which the abnormal shadow can be present is present on the straight line.

Another radiographic image display method according to the present invention includes: detecting an abnormal shadow from each of two radiographic images, which are acquired by radiographing a subject from two different directions in order to display a stereo image, and a third radiographic image having a different radiographing direction from the two radiographic images; displaying one of the two radiographic images; receiving designation of a desired abnormal shadow in the one radiographic image; specifying an abnormal shadow, which corresponds to the designated abnormal shadow, in the other radiographic image, which is different from the one radiographic image, based on positional relationship of abnormal shadows in the two radiographic images and the third radiographic image; and displaying the stereo image while displaying a cursor in a three-dimensional manner at a position of the designated abnormal shadow.

According to the present invention, when a plurality of abnormal shadows are detected in two radiographic images for displaying a stereo image, a cursor is displayed in a three-dimensional manner at the position of a predetermined abnormal shadow of the plurality of abnormal shadows when displaying the stereo image. In addition, when there is an instruction to change the position of the cursor, the cursor is sequentially moved to each position of the plurality of abnormal shadows. For this reason, the operator does not need to perform an operation to move a cursor in both a planar direction and a depth direction in order to designate an abnormal shadow on a stereo image. As a result, the cursor can be easily moved to the position of an abnormal shadow.

In addition, since there is no need to continuously watch the stereo image for a long period of time in order to match the sense of depth of a three-dimensional cursor with the sense of depth of an abnormal shadow, eye fatigue of the operator can be reduced.

In addition, by specifying abnormal shadows corresponding to each other in a plurality of abnormal shadows, a cursor can be reliably moved to one abnormal shadow when displaying a stereo image.

In addition, by detecting an abnormal shadow from the third radiographic image having a different radiographing direction from the two radiographic images and specifying abnormal shadows corresponding to each other based on the positional relationship of the abnormal shadows in the two radiographic images and the third radiographic image, abnormal shadows corresponding to each other can be reliably specified even when abnormal shadows corresponding to each other cannot be specified if only two radiographic images are used.

In addition, according to another aspect of the present invention, when designation of a desired abnormal shadow in one radiographic image displayed in a two-dimensional manner is received, an abnormal shadow corresponding to the designated abnormal shadow in the other radiographic image, which is different from one radiographic image, is specified based on the positional relationship of abnormal shadows in the two radiographic images and the third radiographic image. In addition, the stereo image is displayed in a three-dimensional manner, and the cursor is displayed in a three-dimensional manner at the position of the designated abnormal shadow. Here, since a depth direction does not need to be taken into consideration in the radiographic image displayed in a two-dimensional manner, an abnormal shadow can be easily designated.

Therefore, according to another aspect of the present invention, the operator does not need to perform an operation to move a cursor in both a planar direction and a depth direction. As a result, the cursor can be easily moved to the position of an abnormal shadow. In addition, by detecting an abnormal shadow from the third radiographic image having a different radiographing direction from the two radiographic images and specifying abnormal shadows corresponding to each other based on the positional relationship of the abnormal shadows in the two radiographic images and the third radiographic image, abnormal shadows corresponding to each other can be reliably specified even when abnormal shadows corresponding to each other cannot be specified if only two radiographic images are used.

DESCRIPTION OF THE PREFERRED EMBODIMENTS

Figure 1:
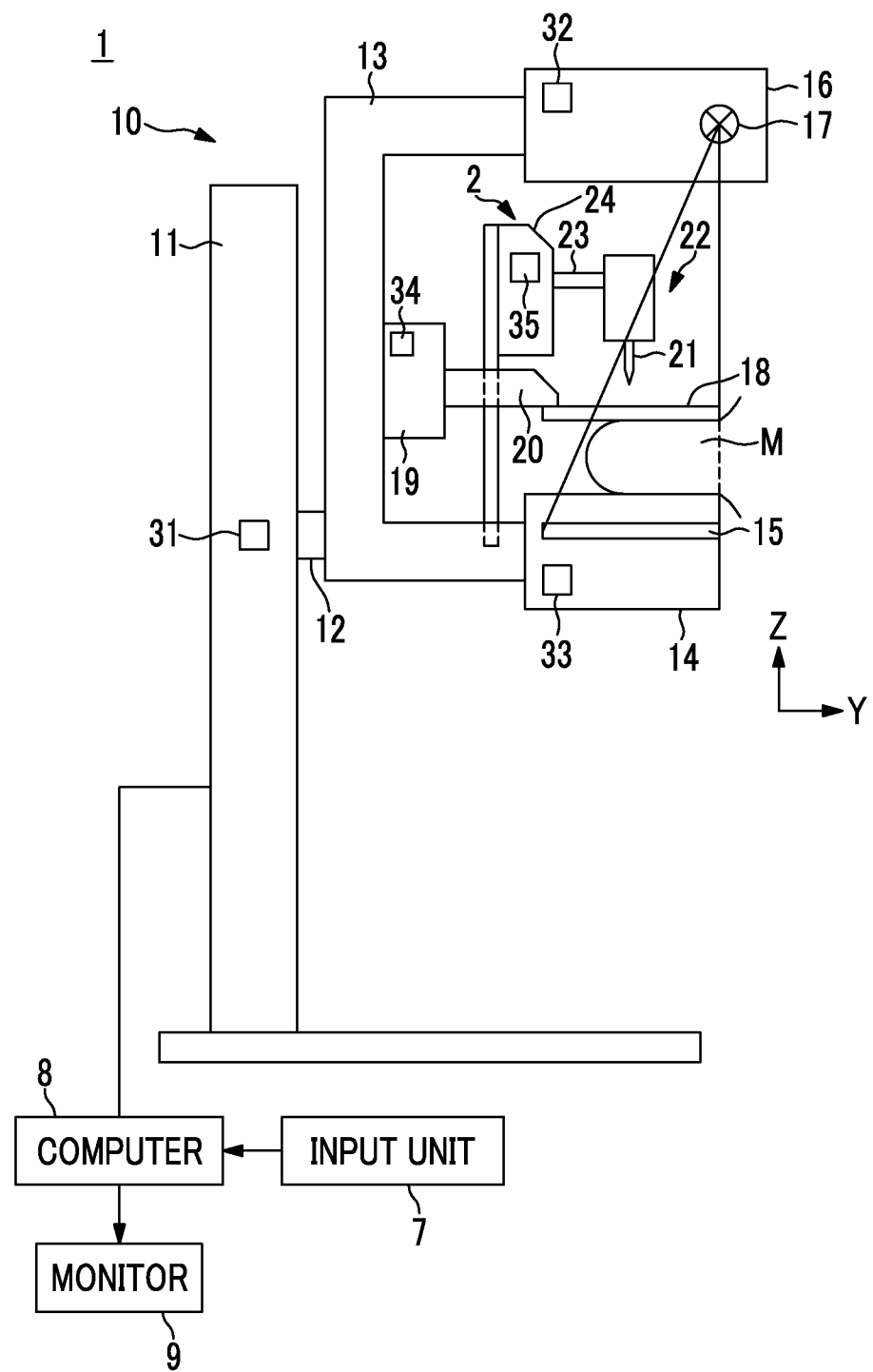
FIG. 1 is a schematic view of the configuration of a stereo breast image radiographing and display system using an embodiment of a radiographic image display device of the present invention.

Hereinafter, a stereo breast image radiographing and display system using an embodiment of a radiographic image display device of the present invention will be described with reference to the drawings. A breast image radiographing and display system according to a first embodiment of the present invention is a system that also operates as a stereo biopsy device for breast by attaching a detachable biopsy unit. First, the schematic configuration of the entire breast image radiographing and display system of the present embodiment will be described. FIG. 1 is a diagram showing the schematic configuration of the breast image radiographing and display system in the first embodiment of the present invention in a state where the biopsy unit is attached.

As shown in FIG. 1, a breast image radiographing and display system 1 of the first embodiment includes a breast image radiographing apparatus 10, a computer 8 connected to the breast image radiographing apparatus 10, a monitor 9 and an input unit 7 connected to the computer 8.

Figure 2:
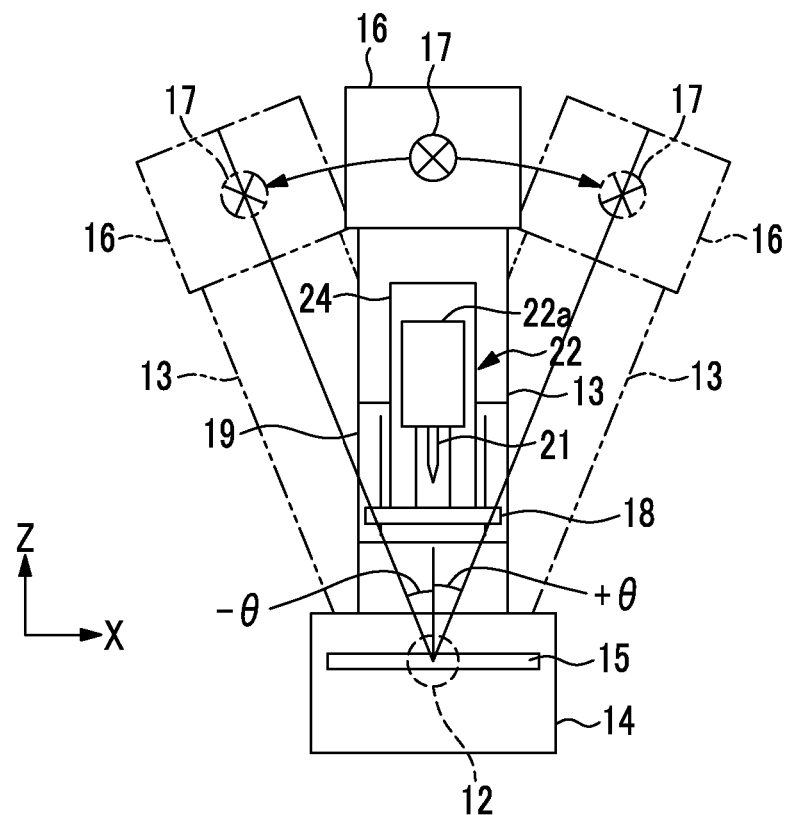
FIG. 2 is a diagram when an arm unit of the stereo breast image radiographing and display system shown in FIG. 1 is viewed from the right direction of FIG. 1.

In addition, as shown in FIG. 1, the breast image radiographing apparatus 10 includes a pedestal 11, a rotary shaft 12 that can rotate and move up and down (in a Z direction) with respect to the pedestal 11, and an arm unit 13 connected to the pedestal 11 by the rotary shaft 12. In addition, FIG. 2 shows the arm unit 13 when viewed from the right side of FIG. 1.

The arm unit 13 has a shape of a letter C. A radiation plane 14 is fixed to one end of the arm unit 13, and an irradiation unit 16 is fixed to the other end so as to face the radiation plane 14. Rotation and up-and-down movement of the arm unit 13 are controlled by an arm controller 31 provided in the pedestal 11.

A radiation detector 15, such as a flat panel detector, and a detector controller 33 that controls the reading of a charge signal from the radiation detector 15 are provided inside the radiation plane 14. In addition, a circuit board on which a charge amplifier that converts a charge signal read from the radiation detector 15 into a voltage signal, a correlated double sampling circuit that samples a voltage signal output from the charge amplifier, an AD conversion unit that converts a voltage signal into a digital signal, and the like are also provided inside the radiation plane 14.

In addition, the radiation plane 14 is configured to be able to rotate with respect to the arm unit 13. Accordingly, even when the arm unit 13 rotates with respect to the pedestal 11, the direction of the radiation plane 14 can be fixed with respect to the pedestal 11.

The radiation detector 15 can perform the recording and reading of a radiographic image repeatedly. A so-called direct type radiation detector that generates electric charges by direct reception of radiation may be used, or a so-called indirect type radiation detector that first converts a radiation into visible light and then converts the visible light into a charge signal may be used. In addition, as a method for reading a radiographic image signal, a so-called TFT reading method in which a radiographic image signal is read by ON/OFF of a TFT (thin film transistor) switch or a so-called optical reading method in which a radiographic image signal is read by irradiation of reading light is preferably used. However, other methods may be used without being limited to these methods.

A radiation source 17 and a radiation source controller 32 are housed in the irradiating unit 16. The radiation source controller 32 controls an irradiation timing of radiation from the radiation source 17 and radiation generation conditions (tube current, time, product of tube current and time, and the like) in the radiation source 17.

Figure 3:
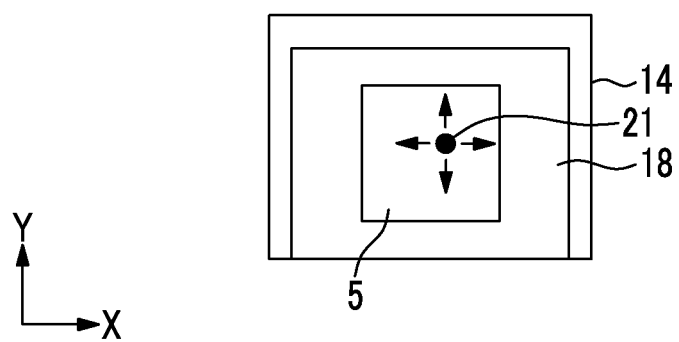
FIG. 3 is a diagram when a radiation plane of the stereo breast image radiographing and display system shown in FIG. 1 is viewed from above.

In addition, a compression plate 18 provided above the radiation plane 14 to compress a breast, a support unit 20 that supports the compression plate 18, and a moving mechanism 19 that moves the support unit 20 up and down (in the Z direction) are provided in the middle of the arm unit 13. The position and the pressure of the compression plate 18 are controlled by a compression plate controller 34. FIG. 3 is a diagram when the compression plate 18 shown in FIG. 1 is viewed from above. As shown in this drawing, the compression plate 18 includes an opening 5 having a size of about 10 cm×10 cm square so as to perform a biopsy in a state where the breast is fixed by the radiation plane 14 and the compression plate 18.

A biopsy unit 2 is mechanically and electrically connected to the breast image radiographing and display system 1 since a base portion of the biopsy unit 2 is inserted into the opening of the support unit 20 of the compression plate 18 and the lower end of the base portion is attached to the arm unit 13.

In addition, the biopsy unit 2 has a biopsy needle 21 that punctures the breast, and has a biopsy needle unit 22 configured to be detachable, a needle support section 23 that supports the biopsy needle unit 22, and a moving mechanism 24 that moves the needle support section 23 along the rail or moves the biopsy needle unit 22 in the X, Y, and Z directions shown in FIGS. 1 to 3 by moving the needle support section 23 in and out. The position of the tip of the biopsy needle 21 of the biopsy needle unit 22 is controlled by being recognized as position coordinates (x, y, z) in three-dimensional space by a needle position controller 35 provided in the moving mechanism 24. In addition, a direction perpendicular to the plane in FIG. 1 is the X direction, a direction perpendicular to the plane in FIG. 2 is the Y direction, and a direction perpendicular to the plane in FIG. 3 is the Z direction.

Figure 4:
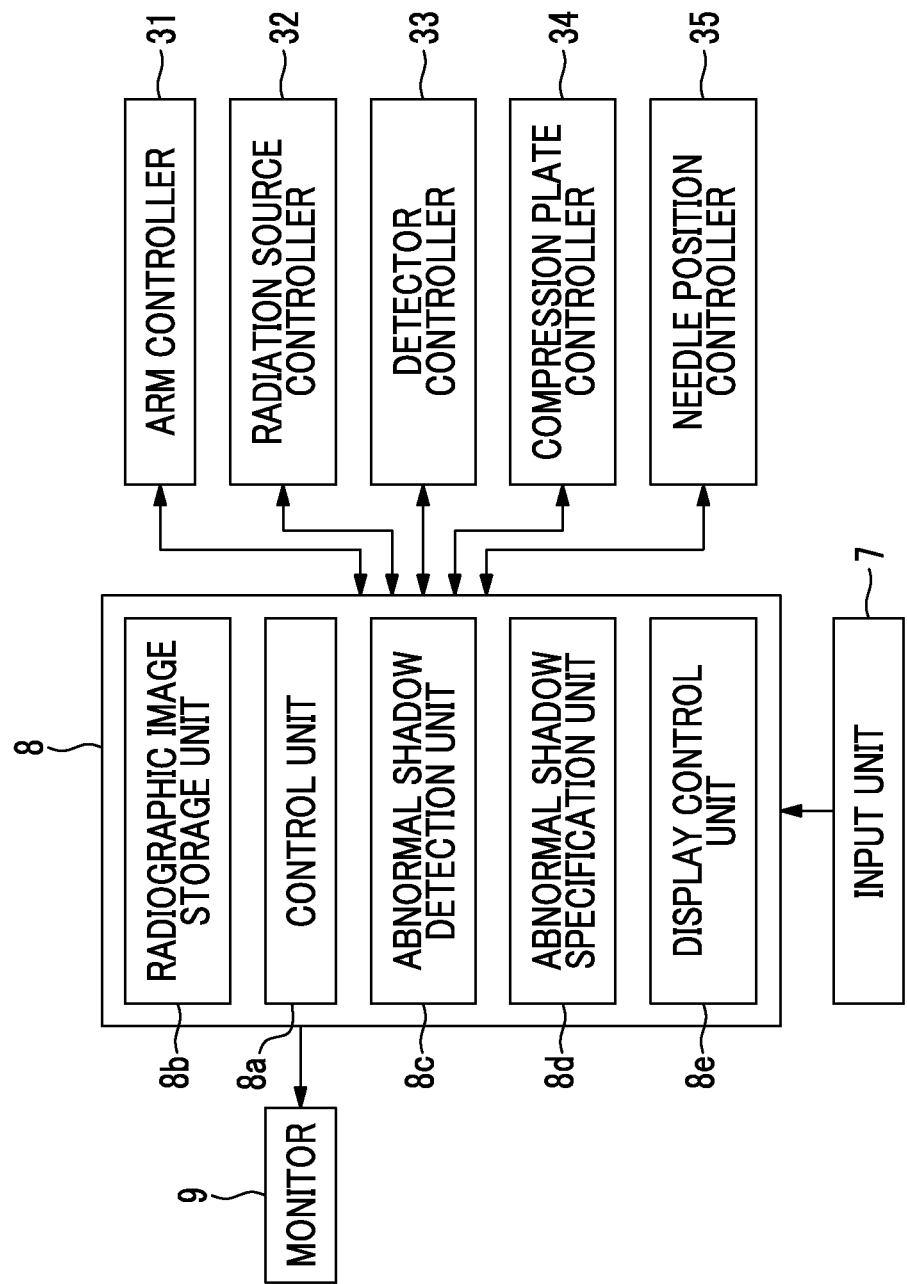
FIG. 4 is a block diagram showing the schematic configuration inside a computer of the stereo breast image radiographing and display system shown in FIG. 1.

The computer 8 includes a central processing unit (CPU) and a storage device, such as a semiconductor memory, a hard disk, or an SSD. By such hardware, a control unit 8a, a radiographic image storage unit 8b, an abnormal shadow detection unit 8c, an abnormal shadow specification unit 8d, and a display control unit 8e shown in FIG. 4 are formed. In addition, the control unit 8a also functions as a warning unit in the present invention.

The control unit 8a outputs predetermined control signals to various kinds of controllers 31 to 35 to control the entire system. A specific control method will be described later.

The radiographic image storage unit 8b stores a radiographic image signal at each radiation angle acquired by the radiation detector 15.

The abnormal shadow detection unit 8c automatically detects the position of the abnormal shadow within the breast included in a radiographic image by analyzing the radiographic image expressed by the radiographic image signal at each radiation angle. In addition, as an abnormal shadow detection method, an abnormal shadow may be detected based on the characteristics of the concentration distribution or the morphological characteristics of the abnormal shadow. Specifically, an abnormal shadow may be detected using an iris filtering process suitable for mainly detecting a tumor shadow (refer to the above JP1998-97624A (JP-H10-97624A)) or a morphological filtering process suitable for mainly detecting a micro-calcification shadow (refer to the above JP1996-294479A (JP-H08-294479A)). In addition, the abnormal shadow detection unit 8c determines the order of abnormal shadows when a plurality of abnormal shadows are detected. The order determination will be described later.

The abnormal shadow specification unit 8*d* specifies corresponding abnormal shadows, which are detected in radiographic images signals at respective radiation angles, between the radiographic image signals at the respective radiation angles.

The display control unit 8*e* displays a stereo image using two radiographic images on the monitor 9, or displays a three-dimensional cursor at the position of the abnormal shadow in the stereo image as will be described later.

The input unit 7 is formed using a keyboard or a pointing device such as a mouse, for example. The input unit 7 is configured to be able to designate the positions of abnormal shadows and the like in the stereo image displayed on the monitor 9 and the radiographic image displayed as a two-dimensional image using a cursor. In addition, the input unit 7 receives an input of radiographing conditions, an input of operation instruction, and the like from an operator.

The monitor 9 displays a stereo image using two radiographic image signals, which are output from the computer 8, in response to the instruction from the display control unit 8*e*. As the configuration, for example, a configuration may be adopted in which radiographic images based on two radiographic image signals are displayed using two screens and one of the radiographic images is incident on the right eye of the observer and the other radiographic image is incident on the left eye of the observer using a half mirror, polarizing glasses, and the like. Alternatively, for example, a configuration may be adopted in which a stereo image is generated by shifting two radiographic images from each other by a predetermined shift amount and displaying them so as to overlap each other and making them observed through the polarizing glasses, or a configuration may be adopted in which a stereo image is generated by displaying two radiographic images on a 3D liquid crystal, through which stereoscopic viewing is possible, as in a parallax barrier method and a lenticular method.

Figure 5:
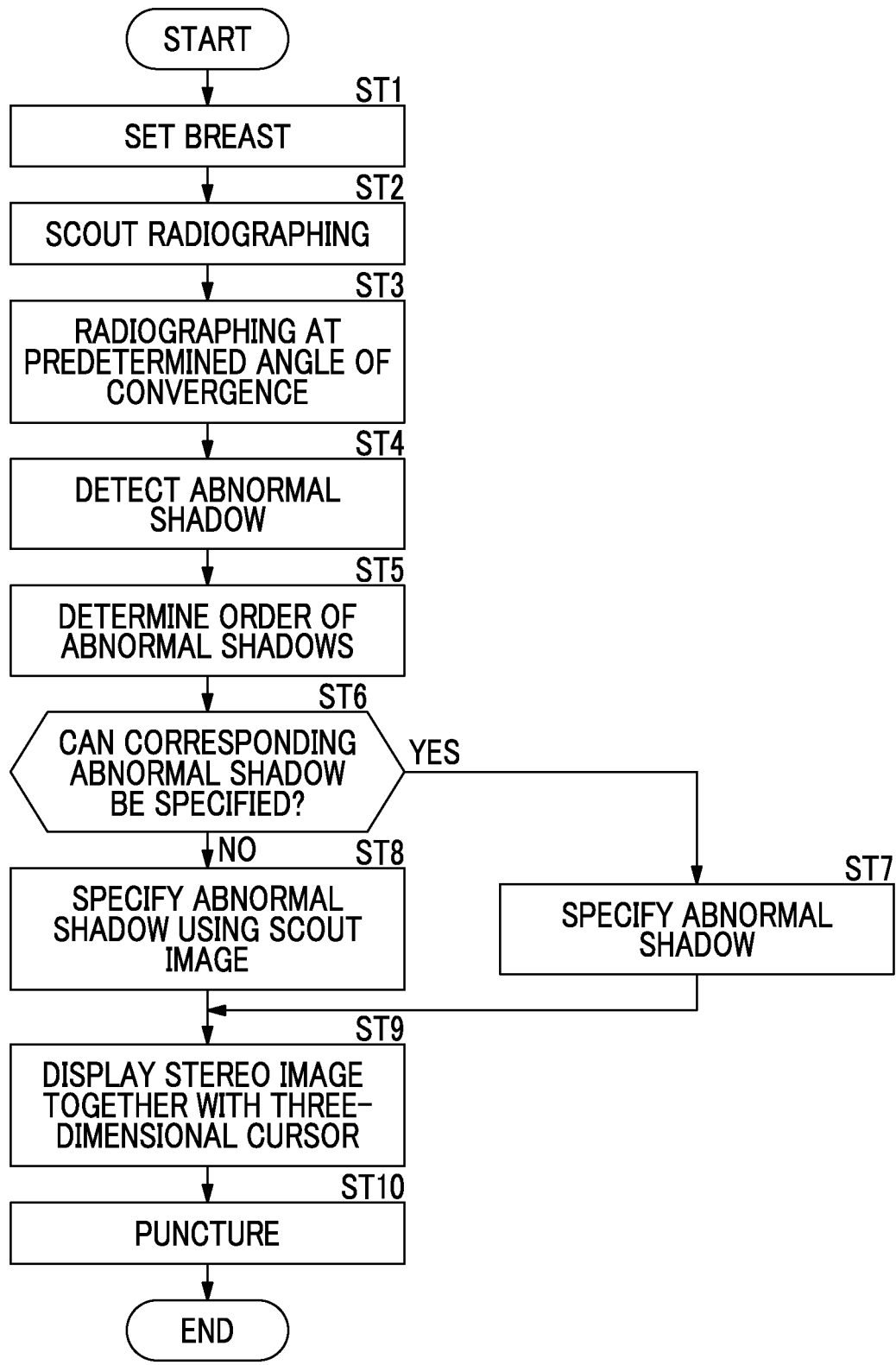
FIG. 5 is a flow chart showing a process performed in a first embodiment.

Next, the operation of the breast image radiographing and display system of the first embodiment will be described with reference to the flow chart shown in FIG. 5.

First, a breast M is placed on the radiation plane 14 and is compressed with predetermined pressure by the compression plate 18 (step ST1).

Then, the operator inputs various radiographing conditions through the input unit 7 and then gives an instruction to start radiographing. In addition, at this time, it is assumed that the biopsy needle unit 22 is retracted upward and the breast has not yet been punctured.

Then, when an instruction to start radiographing is given through the input unit 7, scout radiographing is performed in advance of radiographing a stereo image of the breast M (step ST2). Specifically, first, in order to perform the scout radiographing of the biopsy, the control unit 8*a* outputs a control signal to perform irradiation and reading of a radiographic image signal to the radiation source controller 32 and the detector controller 33. Here, at the initial position of the arm unit 13, the arm unit 13 is at a position perpendicular to the radiation plane 14. Accordingly, in response to this control signal, a radiation is emitted from the radiation source 17, a radiographic image obtained by radiographing the breast from a vertical direction ($\theta=0°$) is detected by the radiation detector 15, a radiographic image signal is read by the detector controller 33, and predetermined signal processing is performed on the radiographic image signal. Then, the radiographic image signal is stored in the radiographic image storage unit 8*b* of the computer 8 as a radiographic image signal of a scout image GS.

The scout image GS acquired by scout radiographing is displayed on the monitor 9. The operator performs positioning of the breast M so that the abnormal shadow visible in the scout image is located at the position of the opening 5 of the compression plate 18 while observing the scout image.

Then, the control unit 8*a* reads an angle of convergence $\theta$ for radiographing of a stereo image set in advance, and outputs the information of the read angle of convergence $\theta$ to the arm controller 31. In addition, in the present embodiment, since a biopsy is performed, it is assumed that $\theta=\pm15°$ is stored in advance as the information of the angle of convergence $\theta$ at this time. However, for example, when a biopsy is not performed, any angle of $\pm2°$ or more and $\pm5°$ or less at which satisfactory stereoscopic viewing is possible may be used without being limited to this.

Then, when an instruction to start radiographing is given through the input unit 7, radiographing of a stereo image of the breast M is performed (step ST3). Then, the arm controller 31 receives the information of the angle of convergence $\theta$ output from the control unit 8*a*. Based on the information of the angle of convergence $\theta$, the arm controller 31 outputs a control signal to rotate the arm unit 13 by $+\theta°$ with respect to the direction perpendicular to the radiation plane 14, as shown in FIG. 2. That is, in the present embodiment, the arm controller 31 outputs a control signal to rotate the arm unit 13 by $+15°$ with respect to the direction perpendicular to the radiation plane 14.

Then, the arm unit 13 rotates by $+15°$ in response to the control signal output from the arm controller 31. Then, the control unit 8*a* outputs a control signal to perform irradiation and reading of a radiographic image signal to the radiation source controller 32 and the detector controller 33. In response to this control signal, a radiation is emitted from the radiation source 17, a radiographic image obtained by radiographing the breast from the direction of $+15°$ is detected by the radiation detector 15, a radiographic image signal is read by the detector controller 33, and predetermined signal processing is performed on the radiographic image signal. Then, the radiographic image signal is stored in the radiographic image storage unit 8*b* of the computer 8. In addition, the radiographic image signal stored in the radiographic image storage unit 8*b* by this radiographing indicates a radiographic image for a right eye GR.

Then, the arm controller 31 returns the arm unit 2 to its initial position as shown in FIG. 2 and then outputs a control signal to rotate the arm unit 13 by $-\theta°$ with respect to the direction perpendicular to the radiation plane 14. In the present embodiment, the arm controller 31 outputs a control signal to rotate the arm unit 13 by $-15°$ with respect to the direction perpendicular to the radiation plane 14.

Then, the arm unit 13 rotates by $-15°$ in response to the control signal output from the arm controller 31. Then, the control unit 8*a* outputs a control signal to perform irradiation and reading of a radiographic image to the radiation source controller 32 and the detector controller 33. In response to this control signal, a radiation is emitted from the radiation source 17, a radiographic image obtained by radiographing the breast M from the direction of $-15°$ is detected by the radiation detector 15, a radiographic image signal is read by the detector controller 33, and predetermined signal processing is performed. Then, the radiographic image signal is stored in the radiographic image storage unit 8*b* of the computer 8. In addition, the radiographic image signal stored in the radiographic image storage unit 8b by this radiographing indicates a radiographic image for a left eye GL.

Then, anesthesia to the breast M is applied, and stereo radiographing is performed again. When the installation position of the breast M is different in the positioning of the breast M before anesthesia and the positioning of the breast M after anesthesia, scout radiographing is performed again. On the other hand, when the installation position of the breast is approximately the same in the positioning of the breast M before anesthesia and the positioning of the breast M after anesthesia, scout radiographing is not performed again in order to reduce the amount of exposure to the subject.

Then, the abnormal shadow detection unit 8c detects an abnormal shadow, such as calcification or a tumor, in the breast from the radiographic image for a left eye GL and the radiographic image for a right eye GR (step ST4). In addition, in the present embodiment, it is assumed that a plurality of abnormal shadows are detected.

Figure 6:
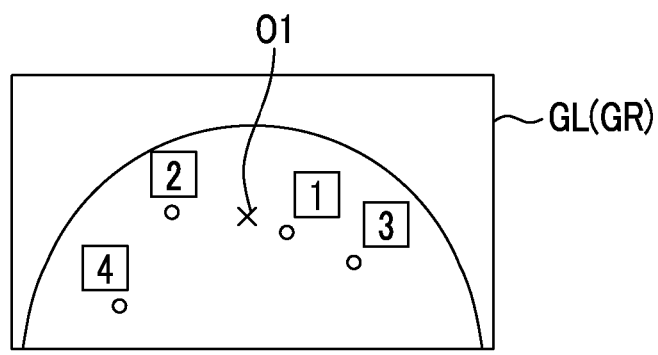
FIG. 6 is a diagram for explaining the determination of the order of a plurality of abnormal shadows.

In addition, the abnormal shadow detection unit 8c determines the order of a plurality of detected abnormal shadows (step ST5). Specifically, as shown in FIG. 6, the center position O1 of the radiographic image for a left eye or a right eye GL (GR) is set, and the order is determined in ascending order of the distance from the center position O1. In addition, since the degree of malignancy of an abnormal shadow becomes high as the output value of the iris filter or the output value of the morphology filter increase, the order may be determined in descending order of the degree of malignancy. In addition, the order of calcification may be increased, or the order of a tumor may be increased conversely. In addition, when a calcification group in which a number of calcification are densely located is present, the order of the group of calcification may be increased (for example, set to No. 1).

Figure 7:
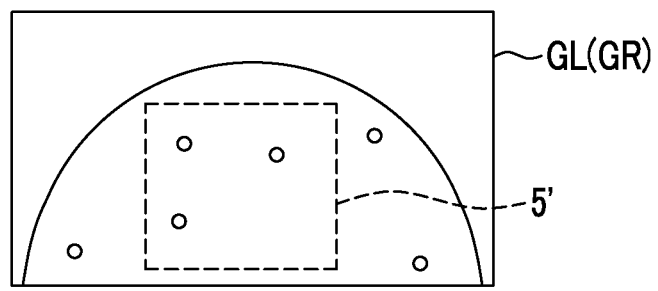
FIG. 7 is a diagram for explaining the determination of the order of a plurality of abnormal shadows.

In addition, in the present embodiment, since a biopsy is performed, the order may be determined only for a plurality of abnormal shadows present in a region 5' corresponding to the opening 5 of the compression plate 18 in the radiographic image GL (GR), as shown in FIG. 7.

Figure 8:
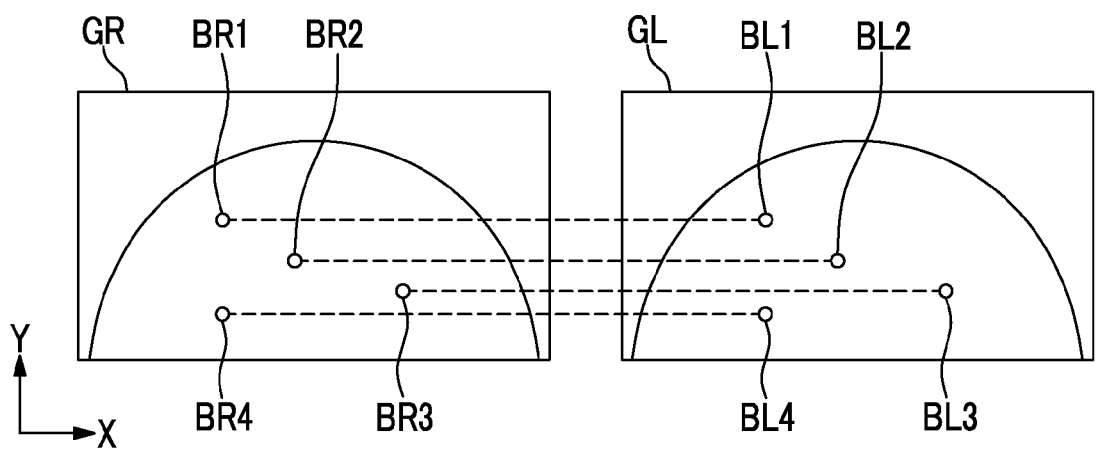
FIG. 8 is a diagram for explaining the specification of a corresponding abnormal shadow.

Then, the abnormal shadow specification unit 8d determines whether or not a corresponding abnormal shadow can be specified by the two radiographic images (step ST6). Hereinafter, the specification of a corresponding abnormal shadow will be described. FIG. 8 is a diagram for explaining the specification of a corresponding abnormal shadow. As shown in FIG. 8, four abnormal shadows BR1 to BR4 are included in the radiographic image for a right eye GR. Here, in the present embodiment, since the movement direction of the radiation source 17 is the X direction shown in FIG. 2, the Y coordinates of the abnormal shadows BR1 to BR4 are the same as the Y coordinates of corresponding abnormal shadows included in the radiographic image for a left eye GL. For this reason, the abnormal shadow specification unit 8d performs a search only in the X direction of the radiographic image for a left eye GL for each of the abnormal shadows BR1 to BR4 included in the radiographic image for a right eye GR, and determines that a corresponding abnormal shadow can be specified by two radiographic images when only one abnormal shadow is present in the radiographic image for a left eye GL. In this case, the corresponding abnormal shadow becomes a searched abnormal shadow (step ST7).

Figure 9:
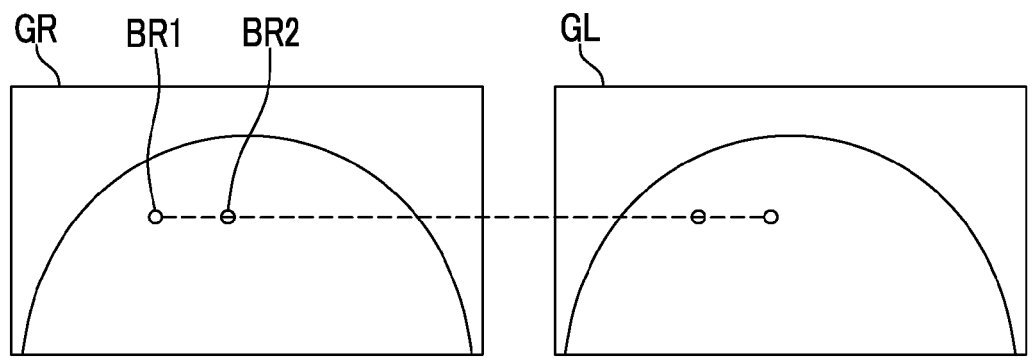
FIG. 9 is a diagram showing a state where a corresponding abnormal shadow cannot be specified.

On the other hand, as shown in FIG. 9, when two abnormal shadows BR1 and BR2 are included in the radiographic image for a right eye GR and the Y coordinates are the same, it is not possible to know which of two abnormal shadows present in the radiographic image for a left eye GL corresponds to the abnormal shadow BR1. For this reason, the abnormal shadow specification unit 8d performs a search only in the X direction of the radiographic image for a left eye GL for the abnormal shadow included in the radiographic image for a right eye GR, and determines that a corresponding abnormal shadow cannot be specified by two radiographic images when two or more abnormal shadows are present in the radiographic image for a left eye GL. In this case, the abnormal shadow specification unit 8d specify a corresponding abnormal shadow using the scout image GS in addition to the two radiographic images GL and GR (step ST8). Hereinafter, the specification of an abnormal shadow using the scout image GS will be described.

Figure 10:
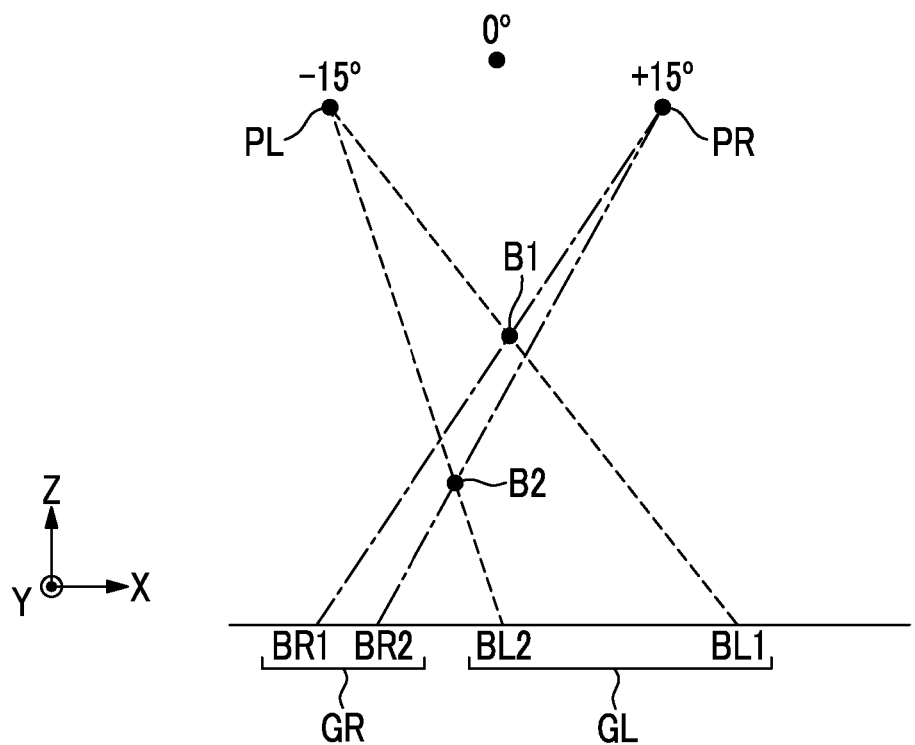
FIG. 10 is a diagram showing a state where a corresponding abnormal shadow cannot be specified.

FIG. 10 is a diagram showing a state where an abnormal shadow cannot be specified. As shown in FIG. 10, when abnormal shadows B1 and B2 are present in the breast, they are included as abnormal shadows BL1 and BL2 in the radiographic image for a left eye GL and as abnormal shadows BR1 and BR2 in the radiographic image for a right eye GR. However, if the positions of the abnormal shadows B1 and B2 in the Y direction are the same, it is not possible to specify to which of the abnormal shadows BR1 and BR2 the abnormal shadow BL1 corresponds and to which of the abnormal shadows BR1 and BR2 the abnormal shadow BL2 corresponds on the radiographic image.

Figure 11:
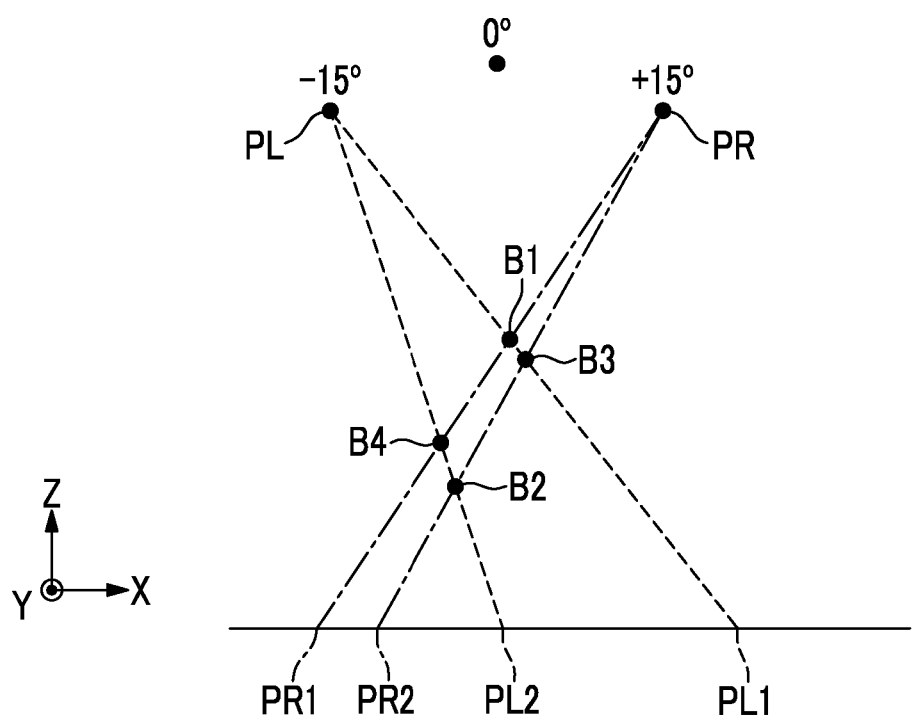
FIG. 11 is a diagram for explaining the specification of an abnormal shadow using a scout image.
Figure 12:
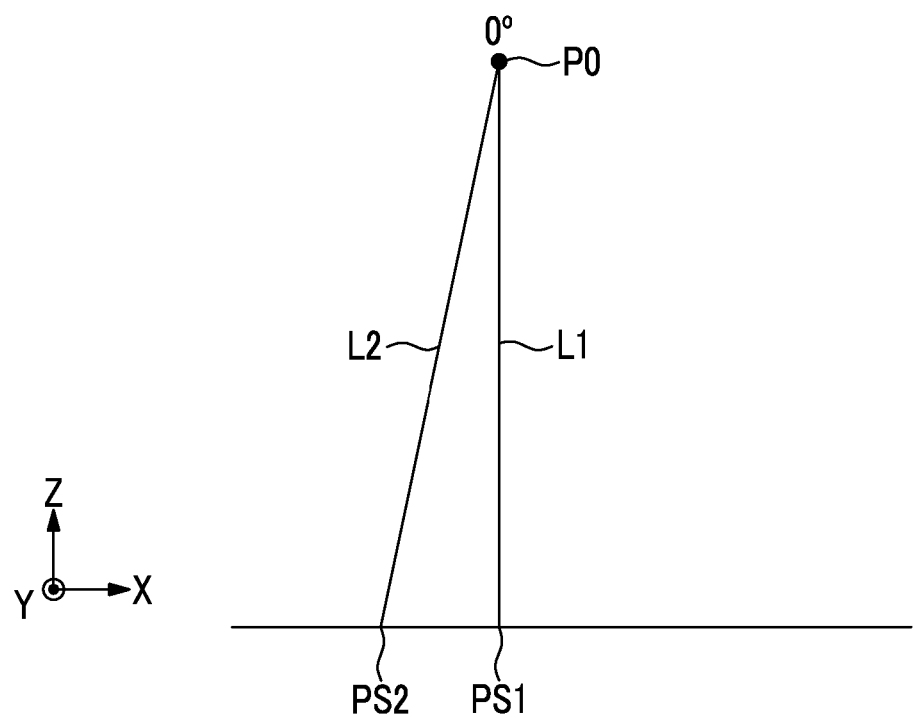
FIG. 12 is a diagram for explaining the specification of an abnormal shadow using a scout image.

FIGS. 11 and 12 are diagrams for explaining the specification of an abnormal shadow using a scout image. In addition, in the following explanation, it is assumed that the Z coordinate of the detection surface of the radiation detector 15 is 0. In addition, it is assumed that the coordinates of abnormal shadows in the radiographic image for a left eye GL are PL1($l1$, 0) and PL2($l2$, 0), the coordinates of abnormal shadows in the radiographic image for a right eye GR are PR1($r1$, 0) and PR2($r2$, 0), the coordinates of the radiation source position PL of $-15°$ are (aL, bL, cL), and the coordinates of the radiation source position PR of $+15°$ are (aR, bR, cR). First, as shown in FIG. 11, the abnormal shadow specification unit 8d sets intersections B1 and B4 between the path of a radiation, which is emitted from the radiation source position PL of $-15°$ and reaches the coordinates PL1 and PL2, and the path of a radiation, which is emitted from the radiation source position PR of $+15°$ and reaches the coordinates PR1, and intersections B2 and B3 between the path of a radiation, which is emitted from the radiation source position PL of $-15°$ and reaches the coordinates PL1 and PL2, and the path of a radiation, which is emitted from the radiation source position PR of $+15°$ and reaches the coordinates PR2. In addition, the coordinates of the positions of the intersections B1 to B4 are calculated using the coordinates PL1($l1$, 0) and PL2($l2$, 0) of the abnormal shadows in the radiographic image for a left eye GL, the coordinates PR1($r1$, 0) and PR2($r2$, 0) of the abnormal shadows in the radiographic image for a right eye GR, the coordinates (aL, bL, cL) of the radiation source position PL of $-15°$, and the coordinates (aR, bR, cR) of the radiation source position PL of $+15°$.

Here, each of the intersections B1 to B4 are on the two straight lines, and the two straight lines are present on the same plane. As shown in FIG. 11, four straight lines passing through the intersections B1 to B4 are straight line PL-PL1, straight line PL-PL2, straight line PR-PR1, and straight line PR-PR2. When each straight line is projected onto the X-Z plane of FIG. 11, each straight line can be expressed as in the following expression.

Straight line $PL\text{-}PL1: z = cL/(aL-l1)*(x-l1)$

Straight line $PL\text{-}PL2: z = cL/(aR-l2)*(x-l2)$

Straight line $PR\text{-}PR1: z = cR/(aR-r1)*(x-r1)$

Straight line $PR\text{-}PR2: z = cR/(aR-r2)*(x-r2)$

In the expressions of the four straight lines, parameters other than x and z are known. Accordingly, the coordinates of the intersections of the four expressions described above can be calculated, and the calculated coordinates of the four intersections become coordinates of the positions of the intersections B1 to B4.

Figure 13:
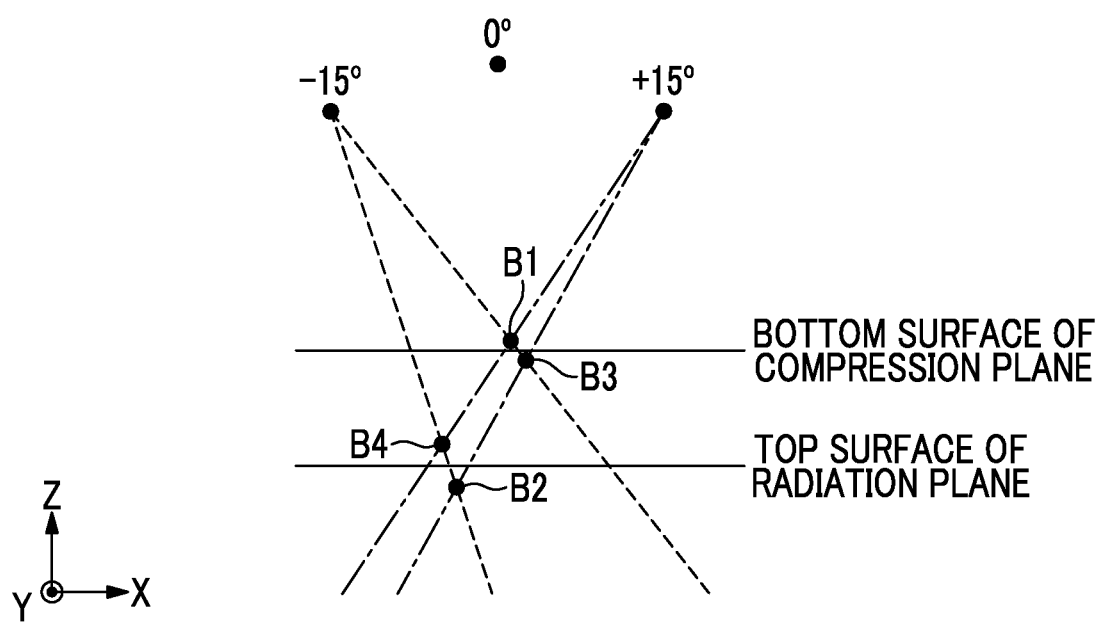
FIG. 13 is a diagram showing a state where a corresponding abnormal shadow can be specified.

In addition, the Z coordinates of the abnormal shadows are neither at positions higher than the bottom surface of the compression plate 18 nor at positions lower than the top surface of the radiation plane 14. For this reason, when the Z coordinates of the calculated intersections B1 to B4 are checked, it can be determined that no abnormal shadow is present at the intersection whose Z coordinate is at a position higher than the bottom surface of the compression plate 18 or at a position lower than the top surface of the radiation plane 14. For example, as shown in FIG. 13, when the Z coordinate of the intersection B1 is at a position higher than the bottom surface of the compression plate or the Z coordinate of the intersection B2 is at a position lower than the top surface of the radiation plane, no abnormal shadow is present at the intersections B1 and B2. In this case, the positions of the intersection B3 and B4 can be specified as positions of abnormal shadows without performing processing to be described later.

Then, the abnormal shadow specification unit 8d calculates an expression Eq1, which indicates a straight line L1 connecting the coordinates PS1($s1$, 0) and the coordinates (aS, cS), and an expression Eq2, which indicates a straight line L2 connecting the coordinates PS2($s2$, 0) and the coordinates (aS, cS), from the coordinates PS1($s1$, 0) and PS2($s2$, 0) of abnormal shadows in the scout image GS and the coordinates (aS, bS, cS) of the radiation source position P0 of 0°. In addition, the expressions Eq1 and Eq2 are calculated by performing projection onto the X-Z plane as in the case of the above expressions of the straight lines passing through the intersections B1 to B4.

$$z = cS/(aS - s1) \times (x - s1) \quad \text{Eq1}$$

$$z = cS/(aS - s2) \times (x - s2) \quad \text{Eq2}$$

In addition, the abnormal shadow specification unit 8d calculates the intersections B1 to B4 present on the straight lines L1 and L2. Specifically, the values of the Z coordinates are calculated by substituting the X coordinates of the intersections B1 to B4 into the expressions Eq1 and Eq2. Then, it is specified which of the intersections B1 to B4 is present on the straight lines L1 and L2 according to whether or not the calculated Z coordinates match the Z coordinates of the intersections B1 to B4. In addition, since the Z coordinates may not completely match each other, it is determined that the Z coordinates match each other with a certain degree of error. Then, the positions of intersections present on the straight lines L1 and L2 are determined to be actual abnormal shadows, and corresponding abnormal shadows are specified in the radiographic image for a left eye GL and the radiographic image for a right eye GR. For example, when the intersection B2 is present on the straight line L1, the coordinates PR2 of the abnormal shadow on the radiographic image for a right eye GR and the coordinates Pl2 of the abnormal shadow on the radiographic image for a left eye GL correspond to each other, and the coordinates PR1 of the abnormal shadow on the radiographic image for a right eye GR and the coordinates Pl1 of the abnormal shadow on the radiographic image for a left eye GL correspond to each other.

Figure 14:
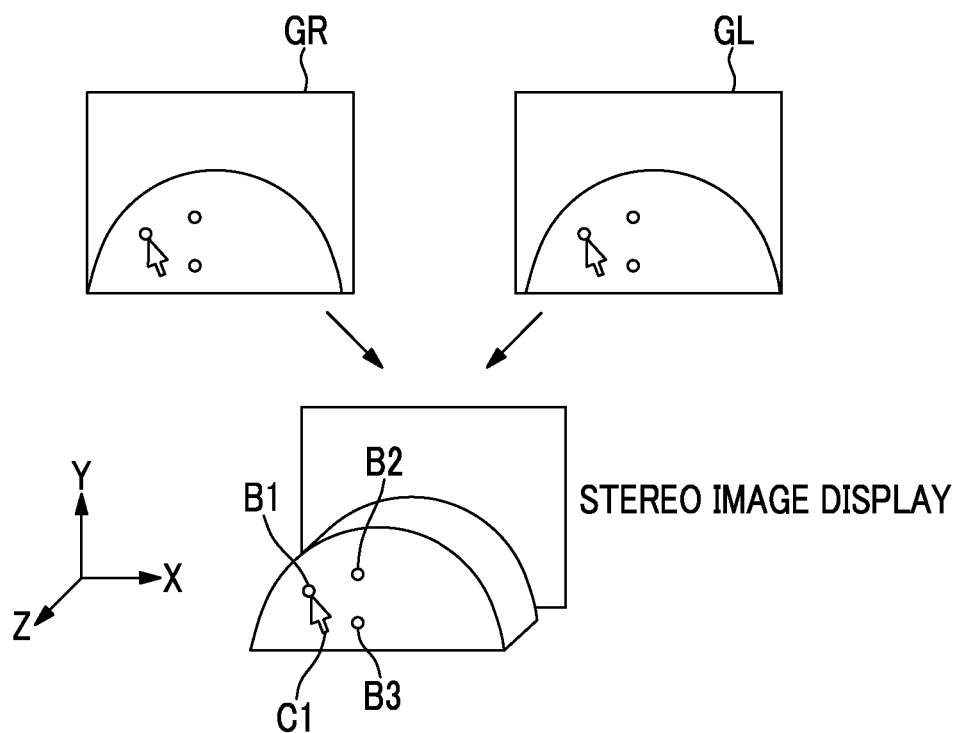
FIG. 14 is a schematic diagram showing a radiographic image and a stereo image displayed on a monitor.

Then, the display control unit 8e reads the two radiographic images GL and GR stored in the radiographic image storage unit 2b, gives a cursor to each position of an abnormal shadow, which has a top order determined, of the abnormal shadows included in the radiographic images GL and GR shown in FIG. 14, and displays a stereo image of the radiographic images GL and GR given with the cursor in a three-dimensional manner on the monitor 9 (step ST9). In this manner, in the stereo image displayed on the monitor 9, a three-dimensional cursor having the same stereoscopic effect as an abnormal shadow is displayed at the position of the abnormal shadow (in FIG. 14, B1).

Figure 15:
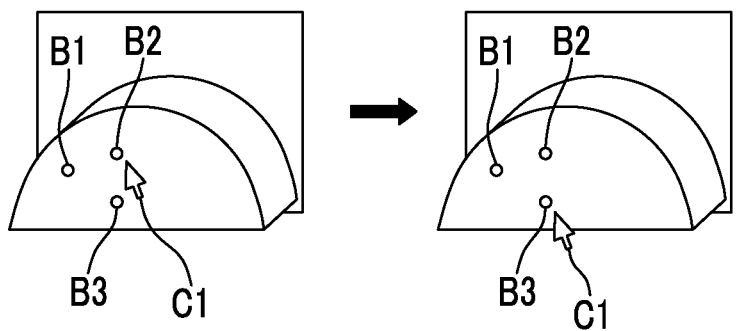
FIG. 15 is a diagram for explaining the movement of a three-dimensional cursor.

Then, the operator can change the position of the three-dimensional cursor by operating the input unit 7. For example, assuming that the order determined by the abnormal shadow detection unit 8c is B1, B2, and B3 for three abnormal shadows B1 to B3 shown in FIG. 14, the position of the three-dimensional cursor C1 is sequentially moved to the abnormal shadow B2 and B3 by the display control unit 8e according to the operation of the input unit 7, as shown in FIG. 15. In addition, after the three-dimensional cursor C1 moves to the abnormal shadow B3, the three-dimensional cursor returns to the position of the abnormal shadow B1 again.

When an abnormal shadow to be the target of a biopsy is designated by moving the three-dimensional cursor C1 as described above, the position information of the target (x, y, z) is acquired by the control unit 8a, and the control unit 8a outputs the position information to the needle position controller 35 of the biopsy unit 2.

When a predetermined operation button in the input unit 7 is pressed in this state, a control signal to move the biopsy needle 21 is output from the control unit 8a to the needle position controller 35. The needle position controller 35 moves the biopsy needle 21 based on the value of the position information input previously so that the tip of the biopsy needle 21 is disposed above the position indicated by the coordinates.

Then, when the observer performs a predetermined operation for instructing the puncture of the biopsy needle 21 through the input unit 7, the biopsy needle 21 is moved so that the tip of the biopsy needle 21 is disposed at the position indicated by the coordinates under the control of the control unit 8a and the needle position controller 35, and the breast is punctured by the biopsy needle 21 (step ST10).

Thus, according to the first embodiment, when a plurality of abnormal shadows are detected in the two radiographic images GL and GR for displaying a stereo image, the three-dimensional cursor C1 is displayed at a position of a predetermined abnormal shadow of the plurality of abnormal shadows and then the three-dimensional cursor C1 is sequentially moved to the positions of the other abnormal shadows in the specified order according to the instruction from the input unit 7 when displaying a stereo image. For this reason, the operator does not need to perform an operation to move the three-dimensional cursor C1 in both a planar direction and a depth direction in order to designate an abnormal shadow on a stereo image. As a result, the three-dimensional cursor C1 can be easily moved to the position of an abnormal shadow.

In addition, since there is no need to continuously watch the stereo image for a long period of time in order to match the sense of depth of a three-dimensional cursor with the sense of depth of an abnormal shadow, eye fatigue of the operator can be reduced.

In addition, in the first embodiment described above, no abnormal shadow may be detected from a radiographic image by the abnormal shadow detection unit 8c. In this case, it is preferable to notify that no abnormal shadow has been detected, for example, by displaying it on the monitor 9 at the predetermined timing, for example, at the time of display of a stereo image. When no abnormal shadow is detected, a three-dimensional cursor may not be displayed or may be displayed at a position set in advance, such as in the middle of an image. In addition, when one abnormal shadow is detected by the abnormal shadow detection unit 8c, a cursor may be given to the position of the abnormal shadow, and the position of the cursor is not changed even if there is an instruction from the input unit 7 or it may be displayed on the monitor 9 that the number of abnormal shadows is one.

In addition, although the radiographic image signals obtained by radiographing at the angle of convergence θ=±15° are used in the first embodiment described above, the present invention is not limited to this. For example, when a biopsy is not performed, radiographing may be performed at any angle of convergence, such as ±2°. In this case, since scout radiographing is not performed unlike a biopsy, the following process is performed when the determination in step ST6 of the first embodiment is NO. Hereinafter, this will be described as a second embodiment.

Figure 16:
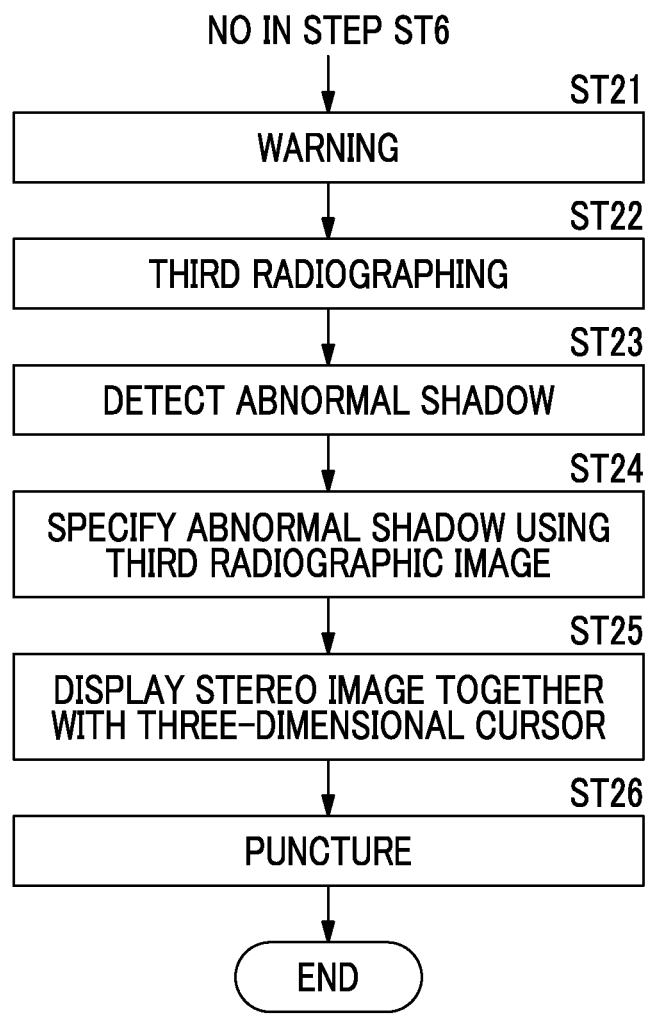
FIG. 16 is a flow chart showing a process performed in a second embodiment.

FIG. 16 is a flow chart showing a process performed in the second embodiment. In addition, FIG. 16 shows only the process after the determination in step ST6 of the flow chart shown in FIG. 5 is NO. When the determination in step ST6 is NO, the control unit 8a gives warning for performing third radiographing from a radiographing direction of a third angle that is different from the angle of convergence θ at which the radiographic image GL for a left eye and the radiographic image GR for a right eye are acquired (step ST21). In addition, as warning, an instruction to perform the third radiographing may be displayed on the monitor 9. In addition, a voice may be used, or both the display on the monitor 9 and the voice may be used.

Thus, an instruction to start the third radiographing is input through the input unit 7 by the operator. Then, if there is an instruction to start radiographing through the input unit 7, third radiographing of the breast M is performed (step ST22). In the third radiographing, the control unit 8a reads an angle for the third radiographing and outputs the information of the angle to the arm controller 31. Then, the arm controller 31 receives the information of the third angle output from the control unit 8a. Based on this information of the third angle, the arm controller 31 outputs a control signal to rotate the arm unit 13 by the third angle with respect to the direction perpendicular to the radiation plane 14.

Then, the arm unit 13 rotates by the third angle in response to the control signal output from the arm controller 31. Then, the control unit 8a outputs a control signal to perform irradiation and reading of a radiographic image signal to the radiation source controller 32 and the detector controller 33. In response to this control signal, a radiation is emitted from the radiation source 17, a radiographic image obtained by radiographing the breast from the direction of the third angle is detected by the radiation detector 15, a radiographic image signal is read by the detector controller 33, and predetermined signal processing is performed on the radiographic image signal. Then, the radiographic image signal is stored in the radiographic image storage unit 8b of the computer 8.

Then, the abnormal shadow detection unit 8c detects an abnormal shadow from the radiographic image (referred to as a third radiographic image) obtained by radiographing from the direction of the third angle (step ST23), and the abnormal shadow specification unit 8d specifies the abnormal shadow using the third radiographic image (step ST24). In addition, since specific processing on the abnormal shadow is performed using the third radiographic image instead of the scout image in the first embodiment, detailed explanation thereof will be omitted herein.

Then, a stereo image is displayed together with a three-dimensional cursor as in step ST9 of the first embodiment (step ST25), and the breast is punctured by the biopsy needle 21 (step ST26).

Next, a third embodiment of the present invention will be described. The configuration of a breast image radiographing and display system according to the third embodiment is the same as that of the breast image radiographing and display system according to the first embodiment and only the process performed is different, detailed explanation regarding the configuration will be omitted herein.

Figure 17:
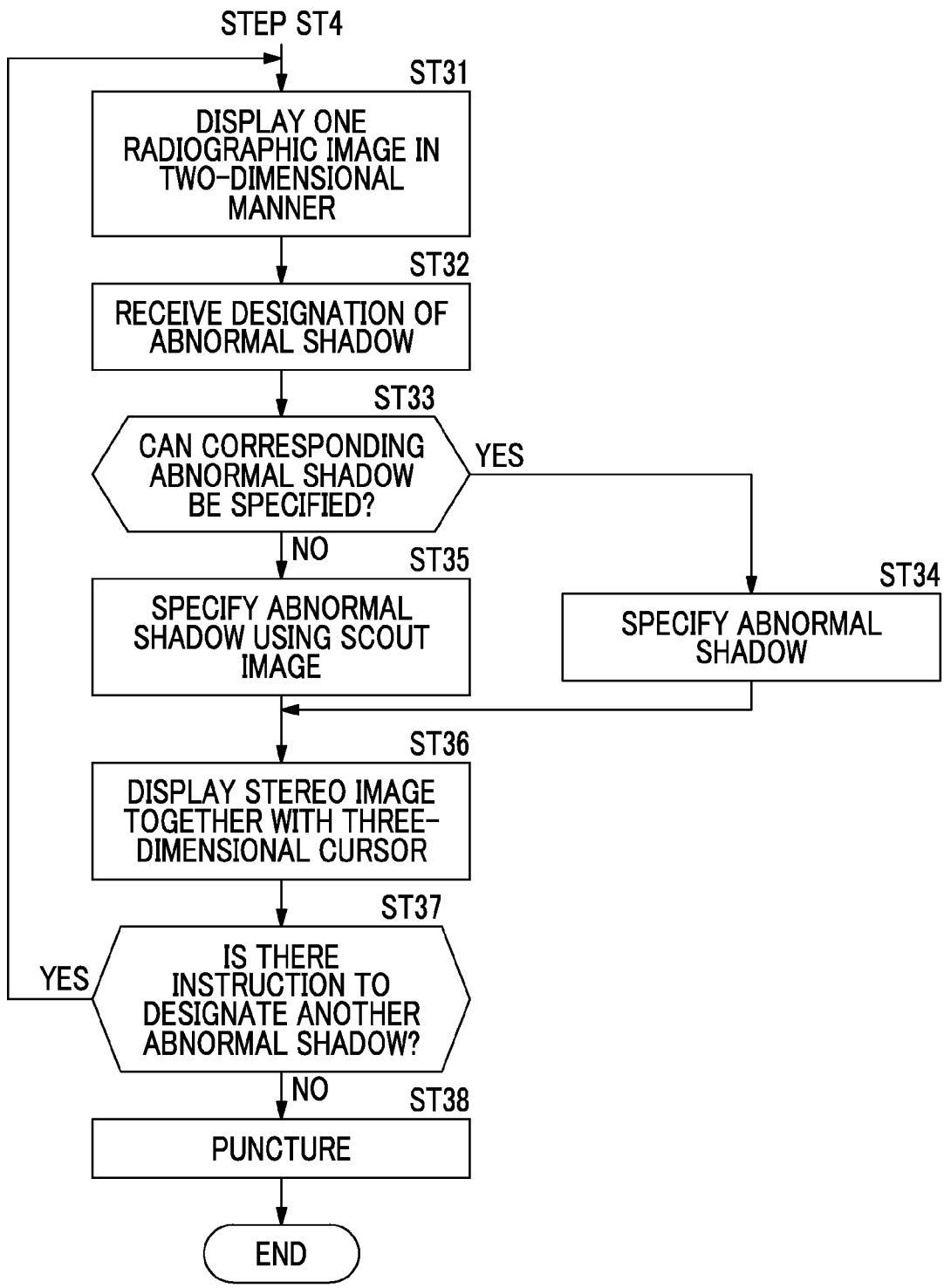
FIG. 17 is a flow chart showing a process performed in a third embodiment.

FIG. 17 is a flow chart showing a process performed in the third embodiment. In addition, FIG. 17 shows only the process after step ST4 of the flow chart shown in FIG. 5.

Figure 18:
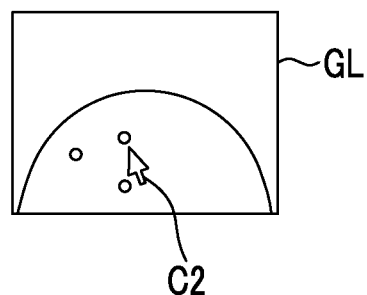
FIG. 18 is a diagram for explaining the designation of an abnormal shadow in the third embodiment.

When an abnormal shadow is detected by the abnormal shadow detection unit 8c, the control unit 8a displays one (for example, the radiographic image for a left eye GL) of the two radiographic images GL and GR on the monitor 9 (step ST31). In addition, this radiographic image is displayed in a two-dimensional manner without a stereoscopic effect. Then, as shown in FIG. 18, the operator designates a desired abnormal shadow from the plurality of abnormal shadows using the input unit 7 (step ST32). In addition, the operator designates a desired abnormal shadow by operating the input unit 7 to move the cursor C2 to the desired position of the abnormal shadow.

Then, the abnormal shadow specification unit 8d specifies an abnormal shadow, which corresponds to the abnormal shadow designated by the operator, in the other radiographic image (radiographic image for a right eye GR).

Specifically, as in step ST6 of the first embodiment, the abnormal shadow specification unit 8d determines whether or not a corresponding abnormal shadow can be specified by two radiographic images (step ST33). When an abnormal shadow can be specified, the corresponding abnormal shadow becomes a searched abnormal shadow as in the first embodiment (step ST34). On the other hand, when an abnormal shadow cannot be specified, the abnormal shadow specification unit 8d specifies an abnormal shadow using a scout image (step ST35).

Figure 19:
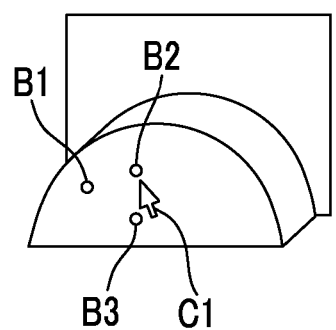
FIG. 19 is a schematic diagram showing a stereo image displayed on a monitor in the third embodiment.

Then, the display control unit 8e reads the two radiographic images GL and GR stored in the radiographic image storage unit 2b, gives a cursor to each position of an abnormal shadow designated in the radiographic image displayed in a two-dimensional manner, and displays a stereo image of the radiographic images GL and GR given with the cursor in a three-dimensional manner on the monitor 9 as shown in FIG. 19 (step ST36). In this manner, a radiographic image of the breast is displayed in a three-dimensional manner, and a three-dimensional cursor C3 having the same stereoscopic effect as an abnormal shadow is displayed in the abnormal shadow (in FIG. 19, B2). In addition, the cursor becomes a three-dimensional cursor.

When the operator wants to designate another abnormal shadow in this state, the operator inputs an instruction to designate another abnormal shadow using the input unit 7 (YES in step ST37). When there is an input of designation of another abnormal shadow, the control unit 8a returns to the process of step ST31.

In this manner, the operator can designate another abnormal shadow other than the abnormal shadow already designated. On the other hand, if there is no designation, when the observer performs a predetermined operation for instructing the puncture of the biopsy needle 21 through the input unit 7, the biopsy needle 21 is moved so that the tip of the biopsy needle 21 is disposed at the position indicated by the coordinates under the control of the control unit 8a and the needle position controller 35, and the breast is punctured by the biopsy needle 21 (step ST38).

Thus, in the third embodiment, when a desired abnormal shadow is designated in one radiographic image displayed in a two-dimensional manner, an abnormal shadow, which corresponds to the designated abnormal shadow, in another abnormal shadow that is different from the radiographic image displayed in a two-dimensional manner is specified based on the positional relationship of abnormal shadows in the two radiographic images and a scout image when necessary, and a cursor is displayed in a three-dimensional manner at the position of the abnormal shadow designated when displaying a stereo image.

For this reason, according to the third embodiment, the operator does not need to perform an operation to move a cursor in both a planar direction and a depth direction in order to designate an abnormal shadow on a stereo image. As a result, the cursor can be easily moved to the position of an abnormal shadow.

In addition, abnormal shadows corresponding to each other are specified using a scout image. Therefore, even when abnormal shadows corresponding to each other cannot be specified if only two radiographic images are used, the abnormal shadows corresponding to each other can be reliably specified.

In addition, in the third embodiment described above, radiographic image signals obtained by radiographing at the angle of convergence $\theta=\pm 15°$ are used as in the first embodiment. However, the present invention is not limited to this. For example, when a biopsy is not performed, radiographing may be performed at any angle of convergence, such as $\pm 2°$, as in the second embodiment. In this case, scout radiographing is not performed. Accordingly, when the determination in step ST33 of the third embodiment is NO, it is preferable to perform third radiographing and specify an abnormal shadow using a third image acquired by the third radiographing as in the second embodiment.

In addition, although an embodiment of the radiographic image display device of the present invention has been applied to the stereo breast image radiographing and display system in the embodiments described above, the subject of the present invention is not limited to the breast. For example, the present invention may also be applied to a radiographic image radiographing and display system that radiographs a chest, a head, and the like.

What is claimed is:

1. A radiographic image display device comprising:
   an abnormal shadow detection unit that detects an abnormal shadow from each of two radiographic images acquired by radiographing a subject from two different directions in order to display a stereo image;
   a display unit that displays the stereo image;
   a display control unit that, when a plurality of the abnormal shadows are detected, displays a cursor in a three-dimensional manner at a position of a predetermined abnormal shadow of the plurality of abnormal shadows; and
   an input unit that receives an instruction to change a position of the cursor,
   wherein the display control unit moves the cursor to each position of the plurality of abnormal shadows sequentially in response to the instruction to change the position of the cursor.

2. The radiographic image display device according to claim 1, further comprising:
   an abnormal shadow specification unit that specifies abnormal shadows corresponding to each other, of the plurality of abnormal shadows detected in the two radiographic images, based on the two radiographic images.

3. The radiographic image display device according to claim 2,
   wherein the abnormal shadow specification unit determines whether or not the corresponding abnormal shadows can be specified based on the two radiographic images,
   the abnormal shadow detection unit detects an abnormal shadow from a third radiographic image, which has a different radiographing direction from the two radiographic images, when the corresponding abnormal shadows cannot be specified, and
   the abnormal shadow specification unit specifies the corresponding abnormal shadows based on positional relationship of abnormal shadows in the two radiographic images and the third radiographic image.

4. The radiographic image display device according to claim 3, further comprising:
   a warning unit that gives warning of acquisition of the third radiographic image when the abnormal shadow specification unit cannot specify the corresponding abnormal shadows based on the two radiographic images.

5. The radiographic image display device according to claim 4,
   wherein the abnormal shadow specification unit specifies a position, at which the abnormal shadow can be present, in the subject from positions of abnormal shadows in the two radiographic images and a position of a radiation source when the two radiographic images are acquired, specifies a straight line connecting the position of the radiation source and the position of the abnormal shadow in the third radiographic image from the position of the abnormal shadow in the third radiographic image and the position of the radiation source when the third radiographic image is acquired, and specifies the corresponding abnormal shadows according to whether or not a position at which the abnormal shadow can be present is present on the straight line.

6. The radiographic image display device according to claim 5,
   wherein, when the two radiographic images are radiographic images of a breast radiographed in order to perform a stereo biopsy, the third radiographic image is acquired by scout radiographing of a biopsy.

7. The radiographic image display device according to claim 5,
   wherein the predetermined abnormal shadow is an abnormal shadow satisfying at least one condition of an abnormal shadow located in a middle of the radiographic image, an abnormal shadow of a specific type, a plurality of dense abnormal shadows, and an abnormal shadow obtained from a predetermined detection result by the abnormal shadow detection unit.

8. The radiographic image display device according to claim 4,
   wherein, when the two radiographic images are radiographic images of a breast radiographed in order to perform a stereo biopsy, the third radiographic image is acquired by scout radiographing of a biopsy.

9. The radiographic image display device according to claim 8,
   wherein the predetermined abnormal shadow is an abnormal shadow satisfying at least one condition of an abnormal shadow located in a middle of the radiographic image, an abnormal shadow of a specific type, a plurality of dense abnormal shadows, and an abnormal shadow obtained from a predetermined detection result by the abnormal shadow detection unit.

10. The radiographic image display device according to claim 4,
wherein the predetermined abnormal shadow is an abnormal shadow satisfying at least one condition of an abnormal shadow located in a middle of the radiographic image, an abnormal shadow of a specific type, a plurality of dense abnormal shadows, and an abnormal shadow obtained from a predetermined detection result by the abnormal shadow detection unit.

11. The radiographic image display device according to claim 3,
wherein the abnormal shadow specification unit specifies a position, at which the abnormal shadow can be present, in the subject from positions of abnormal shadows in the two radiographic images and a position of a radiation source when the two radiographic images are acquired, specifies a straight line connecting the position of the radiation source and the position of the abnormal shadow in the third radiographic image from the position of the abnormal shadow in the third radiographic image and the position of the radiation source when the third radiographic image is acquired, and specifies the corresponding abnormal shadows according to whether or not a position at which the abnormal shadow can be present is present on the straight line.

12. The radiographic image display device according to claim 11,
wherein, when the two radiographic images are radiographic images of a breast radiographed in order to perform a stereo biopsy, the third radiographic image is acquired by scout radiographing of a biopsy.

13. The radiographic image display device according to claim 11,
wherein the predetermined abnormal shadow is an abnormal shadow satisfying at least one condition of an abnormal shadow located in a middle of the radiographic image, an abnormal shadow of a specific type, a plurality of dense abnormal shadows, and an abnormal shadow obtained from a predetermined detection result by the abnormal shadow detection unit.

14. The radiographic image display device according to claim 3,
wherein the predetermined abnormal shadow is an abnormal shadow satisfying at least one condition of an abnormal shadow located in a middle of the radiographic image, an abnormal shadow of a specific type, a plurality of dense abnormal shadows, and an abnormal shadow obtained from a predetermined detection result by the abnormal shadow detection unit.

15. The radiographic image display device according to claim 3,
wherein, when the two radiographic images are radiographic images of a breast radiographed in order to perform a stereo biopsy, the third radiographic image is acquired by scout radiographing of a biopsy.

16. The radiographic image display device according to claim 15,
wherein the predetermined abnormal shadow is an abnormal shadow satisfying at least one condition of an abnormal shadow located in a middle of the radiographic image, an abnormal shadow of a specific type, a plurality of dense abnormal shadows, and an abnormal shadow obtained from a predetermined detection result by the abnormal shadow detection unit.

17. The radiographic image display device according to claim 15,
wherein, when the two radiographic images are radiographic images of a breast radiographed in order to perform a stereo biopsy, the predetermined abnormal shadow is an abnormal shadow present in a range where a biopsy can be acquired by the stereo biopsy.

18. The radiographic image display device according to claim 2,
wherein the predetermined abnormal shadow is an abnormal shadow satisfying at least one condition of an abnormal shadow located in a middle of the radiographic image, an abnormal shadow of a specific type, a plurality of dense abnormal shadows, and an abnormal shadow obtained from a predetermined detection result by the abnormal shadow detection unit.

19. The radiographic image display device according to claim 1,
wherein the predetermined abnormal shadow is an abnormal shadow satisfying at least one condition of an abnormal shadow located in a middle of the radiographic image, an abnormal shadow of a specific type, a plurality of dense abnormal shadows, and an abnormal shadow obtained from a predetermined detection result by the abnormal shadow detection unit.

20. A radiographic image display method using the radiographic image display device according to claim 1, the method comprising:
detecting an abnormal shadow from each of two radiographic images acquired by radiographing a subject from two different directions in order to display a stereo image;
displaying the stereo image while displaying a cursor in a three-dimensional manner at a position of a predetermined abnormal shadow of the plurality of abnormal shadows when a plurality of the abnormal shadows are detected;
receiving an instruction to change a position of the cursor; and
moving the cursor to each position of the plurality of abnormal shadows sequentially in response to the instruction to change the position of the cursor.

* * * * *